United States Patent [19]
Tihon et al.

[11] Patent Number: 5,335,669
[45] Date of Patent: Aug. 9, 1994

[54] RECTAL PROBE WITH TEMPERATURE SENSOR

[75] Inventors: Claude Tihon, Eden Prairie; Timothy C. Cook, Wayzata; John H. Burton; Ronald Svejkovsky, both of Minnetonka, all of Minn.

[73] Assignee: American Medical Systems, Inc., Minnetonka, Minn.

[21] Appl. No.: 50,922

[22] Filed: Apr. 21, 1993

[51] Int. Cl.⁵ ............................................. A61B 5/00
[52] U.S. Cl. ................................................ 128/736
[58] Field of Search .................. 128/736; 604/117; 606/27–31; 607/96, 113, 138

[56] References Cited

U.S. PATENT DOCUMENTS

| | | | |
|---|---|---|---|
| 3,750,667 | 8/1973 | Pshenichny et al. | 604/117 |
| 4,311,154 | 1/1982 | Sterzer et al. | 128/736 |
| 4,660,560 | 4/1987 | Klein . | |
| 4,932,956 | 6/1990 | Reddy et al. . | |
| 4,932,958 | 6/1990 | Reddy et al. . | |
| 4,946,440 | 8/1990 | Hall | 606/27 |
| 5,007,437 | 4/1991 | Sterzer . | |
| 5,114,423 | 5/1992 | Kasprzyk et al. | 606/27 |
| 5,220,927 | 6/1993 | Astrahan et al. | 128/736 |
| 5,234,004 | 8/1993 | Hascoet et al. | 128/736 |
| 5,249,585 | 10/1993 | Turner et al. | 128/736 |

FOREIGN PATENT DOCUMENTS 9115174 10/1991 PCT Int'l Appl. .

*Primary Examiner*—Max Hindenburg
*Attorney, Agent, or Firm*—Peter C. Richardson; Lawrence C. Akers; Mark Dryer

[57] ABSTRACT

A rectal probe comprising a catheter having a longitudinal axis around which is mounted an inflatable, low pressure, compliant balloon having a temperature element associated with the wall thereof, means for holding the probe at a proper position within a patient's rectum and means for inflating the balloon when it is properly positioned to put the temperature element in intimate contact with the anterior side of the rectum. A method for monitoring a patient's rectal mucosal temperature during thermal treatment of the patient's prostate is also disclosed.

15 Claims, 6 Drawing Sheets

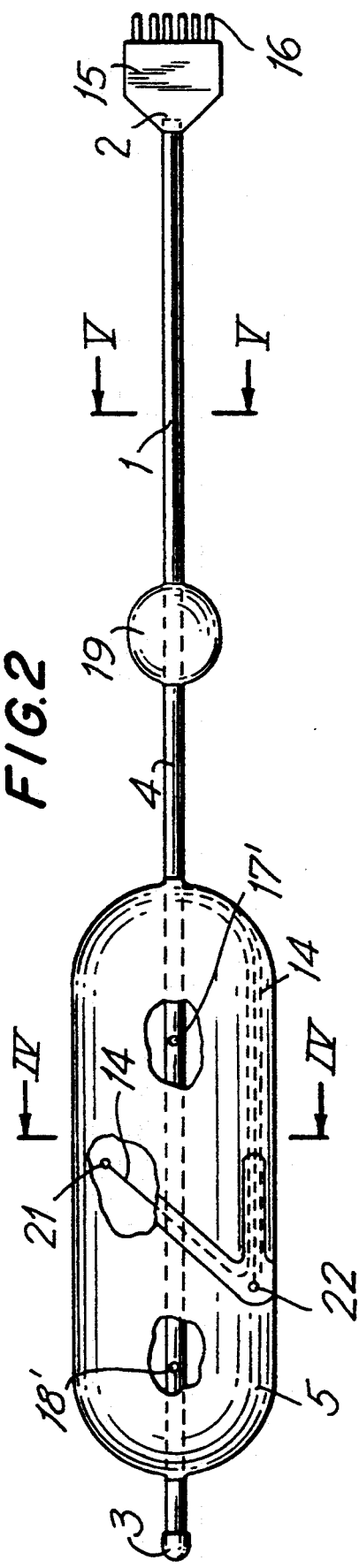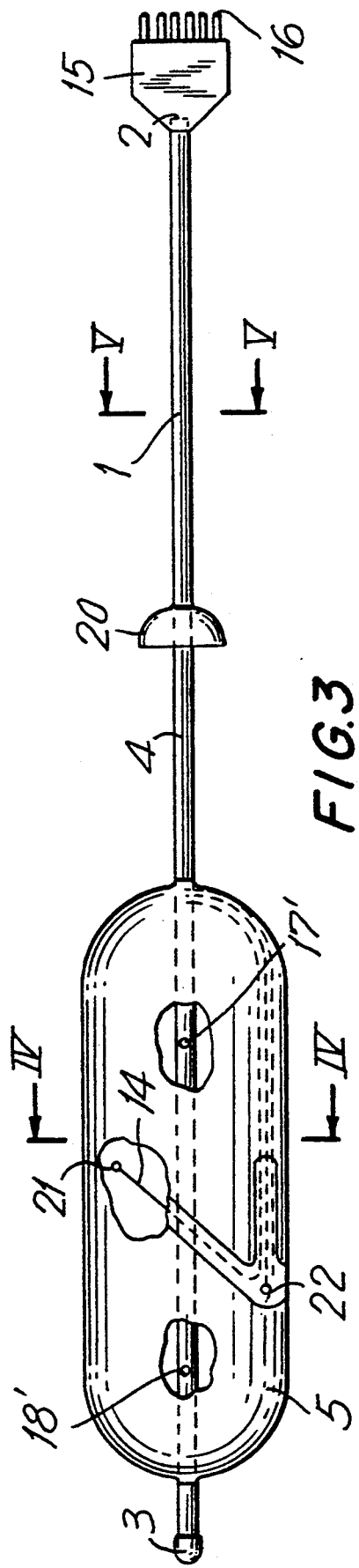

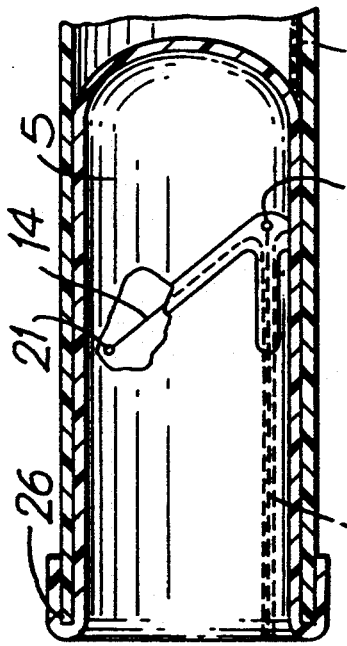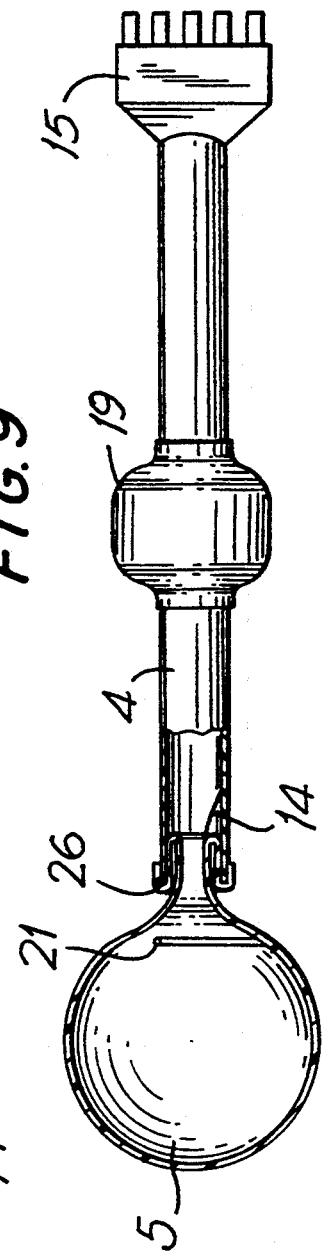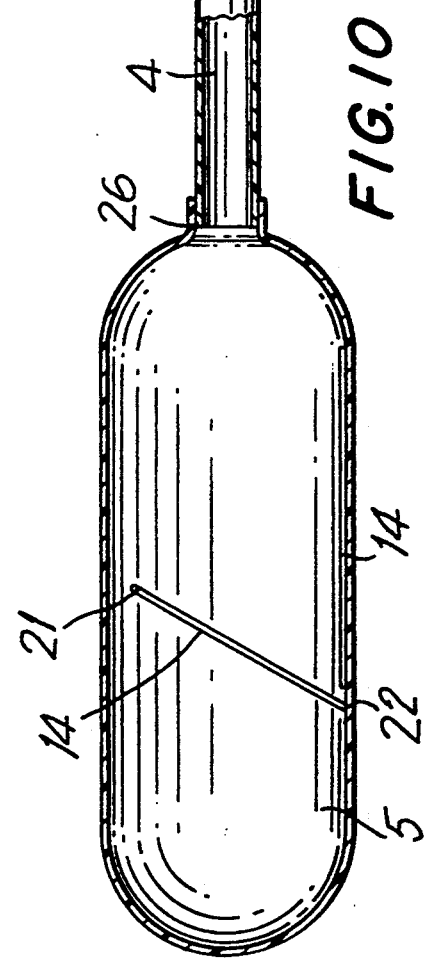

RECTAL PROBE WITH TEMPERATURE SENSOR

FIELD OF INVENTION

This invention relates to a rectal probe, particularly a rectal temperature probe for monitoring transurethral thermal treatment of the prostate. The invention is also concerned with a process for monitoring a patient's rectal mucosal temperature during thermal treatment of the patient's prostate.

BACKGROUND OF THE INVENTION

Various devices for the treatment of disorders of the prostate gland, for example benign prostatic hyperplasia(BPH), are known in the art.

Treatment of obstructive tissue in the prostate urethra with a balloon catheter is disclosed in U.S. Pat. No. 4,660,560 which describes a catheter having a Foley balloon for anchoring the catheter by inflation within the bladder, and an annular balloon for dilation of the prostate urethra.

U.S. Pat. Nos. 4,932,958 and 4,932,956 disclose an apparatus for dilation of the prostate urethra which comprises a catheter for insertion in the prostate urethra having dilation means and spaced-apart location means, the preferred embodiment of the dilation means being an inflatable balloon.

The above devices treat the prostate disorder by dilation of the prostate urethra. Another approach is to treat the prostate by radiant energy. Typical treatments are by electromagnetic radiation, particularly in the microwave range; and by ultrasound. For example, U.S. Pat. No. 5,007,437 discloses a device comprising a catheter adapted to be inserted into the prostate of a male patient, which catheter comprises an inflatable balloon containing a microwave antenna for irradiating the prostate with a given distribution of microwave field intensity, thereby to heat the prostatic tissue. Care has to be taken to limit the maximum microwave power so that the temperature of the heated tissue does not exceed a given safe maximum temperature.

One of the ways to monitor temperature during treatment of the prostate is to utilize a rectal probe containing a temperature sensor.

International Application Publication No. WO 91/15174 discloses a rectal probe having a body made of a flexible, self-supporting polymer wherein the flexibility is defined by a Shore hardness A less then about 90. This publication discloses a therapeutic treatment apparatus which comprises a rectal probe and contains means for hyperthermal treatment of tissue, especially the prostate.

It has now been found that accurate monitoring of temperature during transurethral thermal treatment of the prostate is achieved by the use of a novel rectal probe comprising a balloon catheter having a temperature sensor attached to one wall of the balloon.

SUMMARY OF INVENTION

In accordance with the invention there is provided a rectal probe comprising a catheter having a longitudinal axis, a proximal end and a distal portion terminating in a distal end, an inflatable, low pressure, compliant balloon mounted along said longitudinal axis within said distal portion, a temperature element associated with a side of the balloon wall with leads from said element attached to a connector located at the proximal end of the catheter, means for holding the probe at a proper position within a patient's rectum and means for inflating the balloon, the balloon being inflated when it is properly positioned to put the temperature element in intimate contact with the anterior side of the rectum.

The invention also provides a process for monitoring a patient's rectal mucosal temperature during thermal treatment of the patient's prostate which comprises inserting a rectal probe in the patient's rectum, which probe comprises a catheter having a longitudinal axis, a proximal end and a distal portion terminating in a distal end, an inflatable, low pressure, compliant balloon mounted along said longitudinal axis within said distal portion, a temperature element associated with a side of the balloon wall with leads from said element attached to a connector located at the proximal end of the catheter, means for holding the probe at a proper position within a patient's rectum and means for inflating the compliant balloon, properly positioning the rectal probe so that the temperature element comes into intimate contact with the anterior side of the rectum when the balloon is inflated; inflating the balloon; irradiating the patient's prostate with radiant energy; monitoring the rectal mucosal temperature on the anterior side of the rectum and modulating the radiant energy to prevent over heating leading to rectal injury when a predetermined maximum rectal mucosal temperature is reached. A common rectal injury which might occur without the safeguard of monitoring according to the invention is perforation or ulceration of the rectal wall.

In a preferred embodiment of the probe according to the invention, the temperature element is a thermocouple assembly adapted to monitor rectal mucosal temperature during thermal treatment of the patient's prostate. The assembly may comprise a plurality of thermocouples, for example three, in spaced-apart relationship on one side of the wall of the balloon. The thermocouple assembly may be directly attached to the wall of the balloon, either on the inside or the outside of the wall, so that it is in a fixed position on the wall; or it may be movably associated with the balloon wall, for example by being mounted within a track attached to the wall, so that its position may be adjusted until it is properly positioned for optimum temperature determination. Other types of temperature measurement instruments may be used, for example thermistors, resistant thermometry detectors (RTD) or optical fibers.

The probe according to the invention preferably also includes a hollow tube with an open distal end located along the longitudinal axis. The purpose of the open-ended hollow tube is to allow the release of gas.

The probe also may include cooling means to facilitate cooling of the anterior rectal wall during thermal treatment of the prostate.

In a particularly preferred first embodiment of the invention the means for holding the probe within the patient's rectum is a side arm attached to a housing enveloping a portion of the catheter proximal to the anal sphincter when the compliant balloon is properly positioned for inflation within the rectum. Preferably, the side arm for example a flat flexible arm, is attached to the housing through a longitudinally-movable collar and a lock, for example a cam lock or a screw lock, which enables the arm to be locked in place and taped against the patient's leg when the probe is properly positioned in the patient's rectum.

In a second preferred embodiment the means for holding the probe within the patient's rectum is a second location balloon which stays outside the rectum. In a third embodiment the means for holding the probe within the patient's rectum is a movable ring or tab which is adapted to slide along the axis of the catheter.

In a fourth embodiment of the invention the inflatable compliant balloon, still mounted along the longitudinal axis of the catheter within the distal portion, is contained within the catheter and when inflated is deployed beyond the distal end of the catheter. This embodiment is defined as a rolling diaphragm type.

As used herein the term "properly positioned" means the position wherein the compliant balloon, when inflated to substantially fill the rectum so that the wail of the balloon conforms to the configuration of the walls of the rectum, is orientated so that the temperature element is in intimate contact with the anterior side of the rectum. Since the balloon itself is not visible when it is inserted in the rectum, the orientation thereof is determined by an appropriate marking on the portion of the probe which remains outside the rectum. The relationship between the marking and the mounting of the temperature element is such that when the marking is correctly aligned outside the rectum the temperature element will be properly positioned within the rectum. This proper positioning means that the temperature element, preferably a thermocouple assembly, is at the closest point, within the rectum, to the prostate and thus provides optimum sensitivity for sensing and monitoring temperature during treatment of the prostate. Thus, proper positioning may be confirmed when a maximum temperature reading is provided by the probe. In an alternative embodiment the temperature element itself may be movable relative to the wall of the balloon, and in this embodiment proper positioning is also confirmed by a maximum temperature reading. The low pressure compliant balloon ensures that the probe is conformable to the rectal anatomy so that accurate temperature readings are obtainable.

The manner in which the inflated compliant balloon conforms to the patient's rectal anatomy constitutes a substantial advantage over prior art probes, even those alleged to be "flexible" in that it allows intimate contact between the thermal element and the anterior side of the rectum over the complete surface touched by the balloon so that optimum accurate temperature readings may be consistently obtained.

If desired, any of the above-described embodiments may include means for circulating a coolant, preferably water, within the balloon.

BRIEF DESCRIPTION OF DRAWINGS

Preferred embodiments of the invention are illustrated in the accompanying drawings, in which:

FIG. 2 is a side elevation, with the balloon partially broken away, of a second embodiment;

FIG. 3 is a side elevation, with the balloon partially broken away, of a third embodiment;

FIG. 8 is an enlarged scale section of the distal end of a rolling diaphragm type embodiment;

FIG. 9 is a side elevation of the embodiment of FIG. 8 showing the balloon partially inflated;

FIG. 10 is a side elevation of the distal end of the rolling diaphragm type embodiment with the balloon fully inflated.

FIG. 1 of the drawings illustrates a rectal probe comprising a catheter 1 having a proximal end 2 and a distal end 3. In this first preferred embodiment a hollow tube 4 is located about the longitudinal axis of the catheter and extends from the proximal end to the distal end wherein the open end of the lumen of tube 4 is protected by a cap which is removed before the probe is inserted in a patient's rectum.

An inflatable, low pressure compliant balloon 5 is mounted along the longitudinal axis of the catheter within a distal portion which terminates in the distal end 3. The balloon, when inflated, is compliant and non-tissue deforming and is preferably made from silicone, low-density polyethylene or latex. The size of the compliant balloon is preferably 100–250 FR in diameter with a longitudinal length of about 7 to 20 cm. As shown in FIG. 1, the balloon is in its inflated condition.

Figure 1:
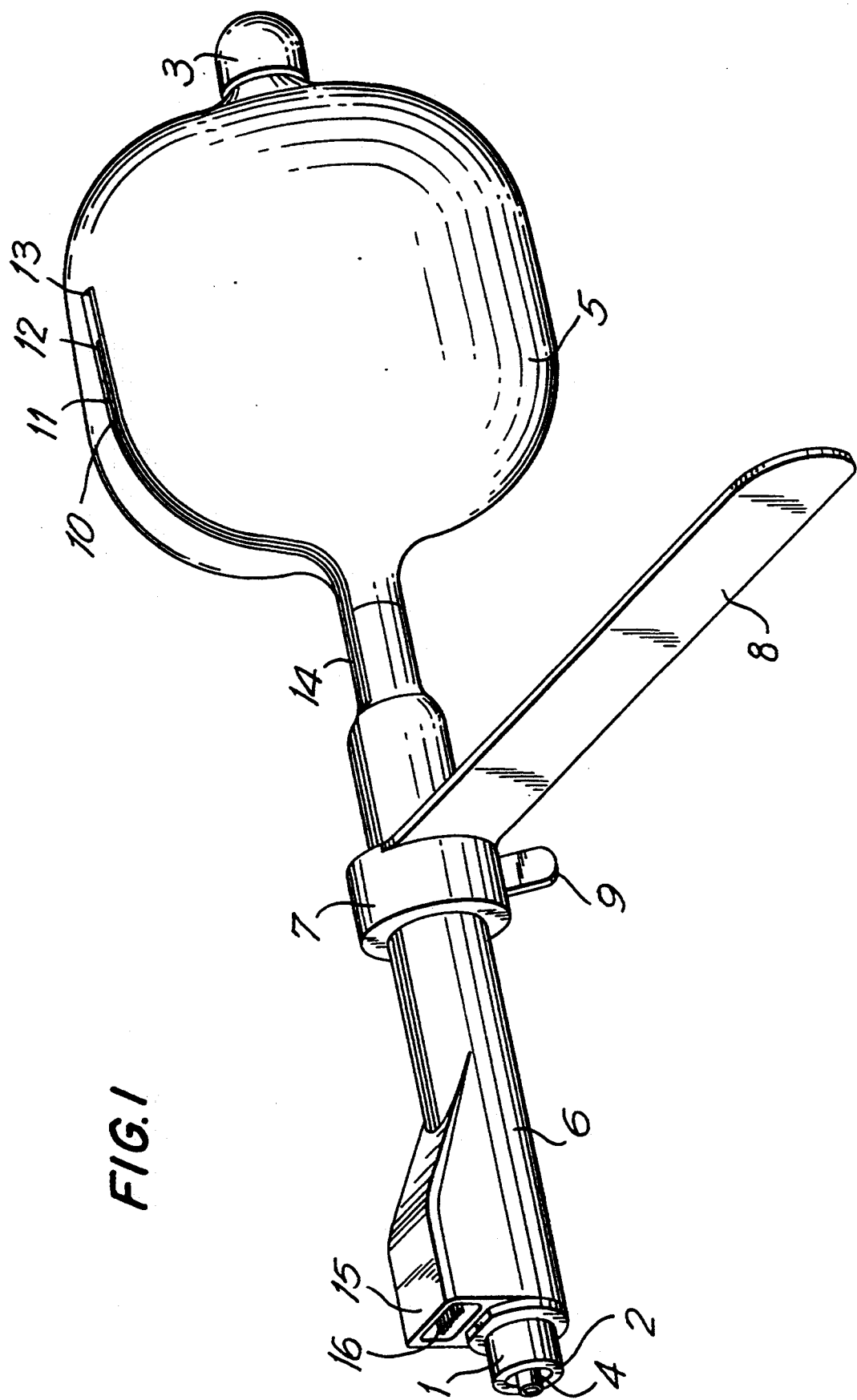
FIG. 1 is a perspective view of a first embodiment with the balloon inflated.

A housing 6 envelopes the catheter adjacent the proximal end thereof and this housing carries a movable collar 7 having an integral flexible arm 8. The flexible arm and collar are adapted to be locked to the housing through a cam lock actuated by a lever 9. A temperature element 10 is attached to a side of the balloon wall. In the first preferred embodiment the temperature element comprises three thermocouples 11, 12, and 13 made from electrically-conducting wires mounted in side-by-side relationship in the form of a flexible ribbon. The lead wires 14 from the thermocouples terminate in a connector 15 mounted on the housing at the proximal end of the catheter. Alternatively, in place of wires, the thermocouples and leads may be formed by thin film metal deposition on the wall of the balloon and the catheter shaft. The connector includes male terminals 16 adapted to be connected, through a complimentary connector with female sockets (not shown), to a cable leading to a monitor for monitoring signals received from the thermocouples.

A second embodiment of the invention is illustrated in FIG. 2 which shows a rectal probe comprising a catheter I having a proximal end 2 and a distal end 3. A cap at the distal end 3 covers the open end of a hollow tube 4 which runs along the full longitudinal axis of the catheter and to which a connector 15 is attached at the proximal end 2. It is to be understood that in each Figure of the drawings the connector, identified by reference numeral 15, is adapted to accommodate through terminals 16, the features associated with the embodiment illustrated as described herein. In each embodiment the general function of connecting the probe to another piece of apparatus is the same, although the number of terminals may differ. The cap is removed before the probe is inserted in a patient's rectum. A compliant inflatable balloon 5 is mounted along the longitudinal axis of the catheter within a distal portion thereof. In FIG. 2, the balloon is shown in inflated condition.

Figure 4:
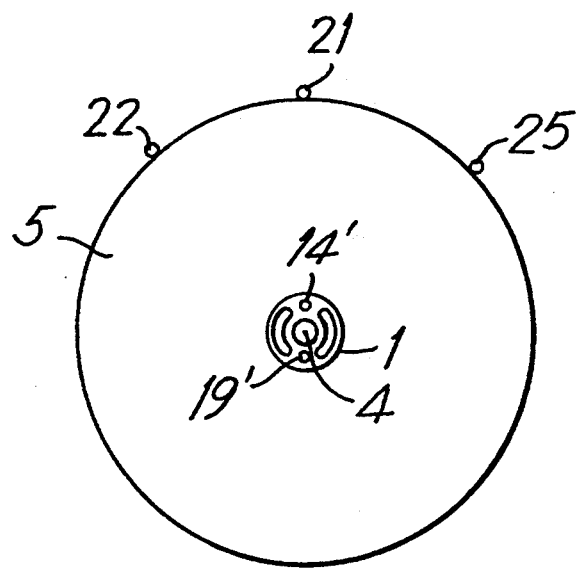
FIG. 4 is a cross-section, on an enlarged scale, through line IV—IV of FIGS. 2 and 3.

Three thermocouples, for example, foil RTDs, are attached to the side of the balloon wall at an overall spacing of 120° in circumferential positioning. Two of these thermocouples 21,22 are shown in FIG. 2. All three, 21, 22, 25 are shown in FIG. 4. Wire leads 14 from the thermocouples pass through the hollow tube 4 to a connector 15 with male terminals 16.

In addition to providing terminals for the leads from the thermocouples, one of the terminals 16 is hollow and provides the proximal vent for the hollow venting tube 4 which allows the venting of gas. The hollow venting tube passes centrally along the axis of the catheter shaft 1 as shown more clearly in the enlarged views of FIG. 4 and FIG. 5.

Figure 5:
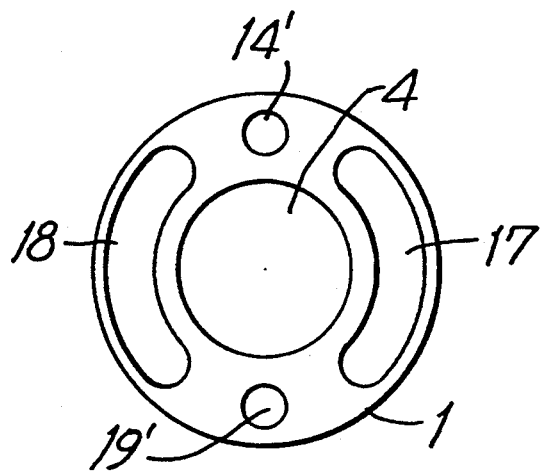
FIG. 5 is a cross-section, on an enlarged scale, through line V—V of FIGS. 2 and 3.

Two other terminals are the proximal ends of means for providing coolant to the balloon. Thus the coolant is passed through lumen 17 along one side of the catheter shaft and enters the balloon at vent 17'. The coolant exits the balloon at vent 18' and passes out through lumen 18, as shown in FIG. 5. The cooling facilitates cooling of the interior rectal wall during thermal treatment of the prostate. Lumen 17 may be used to inflate the balloon or, alternatively, the balloon may be inflated through a separate lumen (not shown).

Instead of the flexible arm 8 and collar 7 shown in FIG. 1, in the second embodiment of FIG. 2, the means for holding the probe within a patient's rectum is a small inflatable location balloon 19, preferably made from the same material as the above described compliant balloon. When inflated, this balloon is located outside the rectum against the entrance to the rectum. The location balloon 19 is inflated through lumen 19' (shown in FIG. 5).

In a third embodiment, illustrated in FIG. 3, the means for holding the probe is a movable tab 20. The third embodiment otherwise includes the features of the second embodiment illustrated in FIG. 2, with the exception of lumen 19' which is no longer required.

Figure 6:
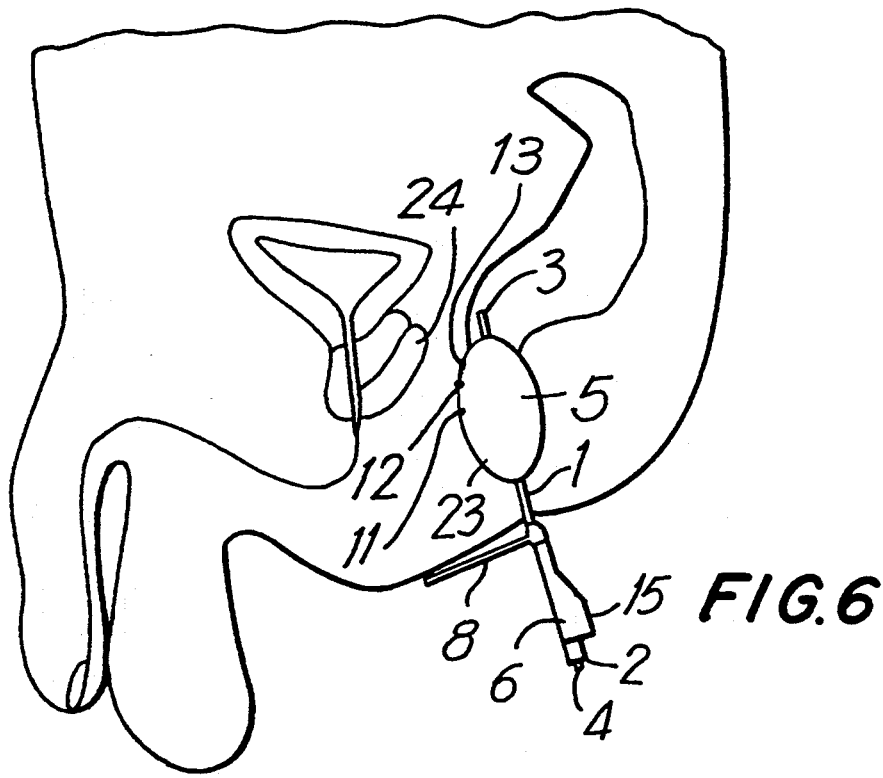
FIG. 6 is a sectional view of a patients anatomy showing a probe as illustrated in FIG. 1 in the inserted position in the rectum.

FIG. 6 illustrates the proper positioning of the probe of FIG. 1 in a patient's rectum 23. The thermocouples 11, 12, 13, are positioned against the anterior side of the rectum for optimum monitoring of the temperature of the anterior rectal wall during thermal treatment of the prostate 24. A particular advantage of this embodiment is that the housing which carries the collar and flexible arm allows manipulation from outside the anus to ensure proper positioning of the probe within the rectum. When the probe is properly positioned in the patient's rectum, the flexible arm 8 is locked in position by lever 9 and may be taped against the patient's leg (not shown).

Figure 7:
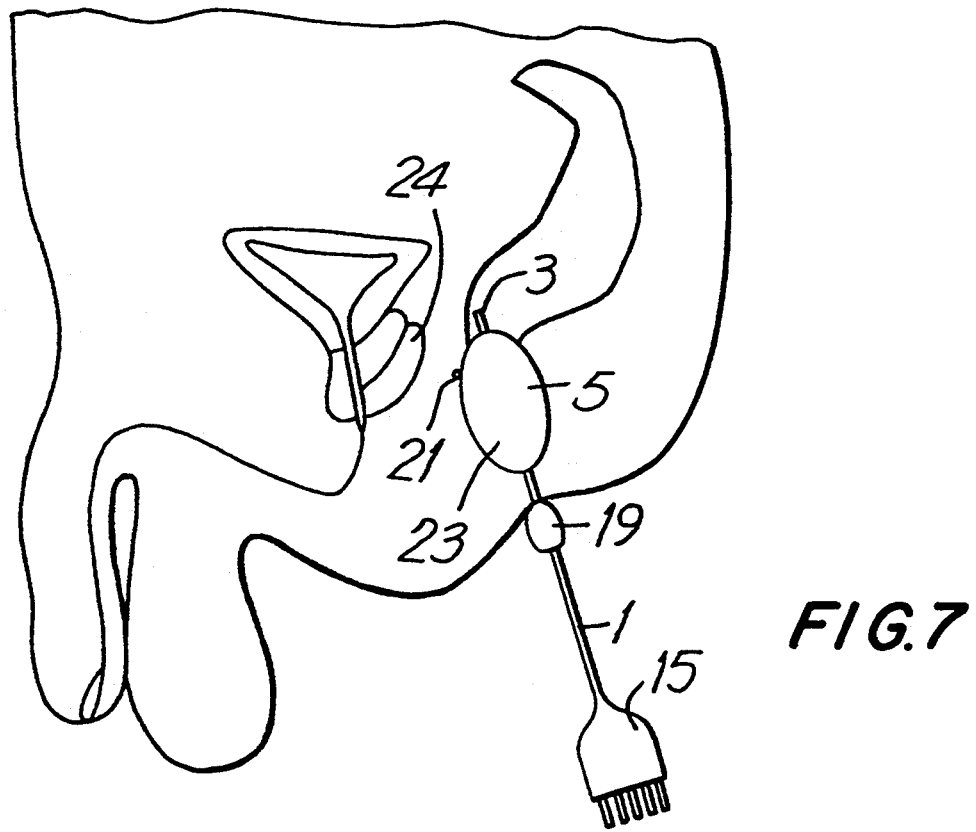
FIG. 7 is a sectional view of a patient's anatomy showing a probe as illustrated in FIG. 2 in the inserted position in the rectum.

FIG. 7 illustrates the proper positioning of a probe as illustrated in FIG. 2 in a patient's rectum. In this operation the location balloon 19 is against the entrance to the rectum.

In order to monitor a patient's rectal mucosal temperature during thermal treatment of the patient's prostate a probe as described above, with the end cap removed and the balloon deflated, is inserted in the patient's rectum. The positioning of the probe is manipulated from outside the anus until the thermocouples on the side of the balloon wall are adjacent the anterior wall of the rectum. The balloon is then inflated so that the thermocouples are in intimate contact with the anterior wall of the rectum and the inflated balloon conforms with the anatomy of the rectum without adverse tissue deformation. When the probe is properly positioned within the rectum it is held in position by locking the holding means as described above.

FIGS. 8–10 illustrate a fourth embodiment of the invention, defined herein as a rolling diaphragm type, in which the inflatable compliant balloon 5 is contained within the distal portion of the catheter so that when it is inflated the balloon is inverted and deployed beyond the distal end 26 of the catheter. In this embodiment the thermocouples are attached to the inside wall of the balloon.

Figure 11:
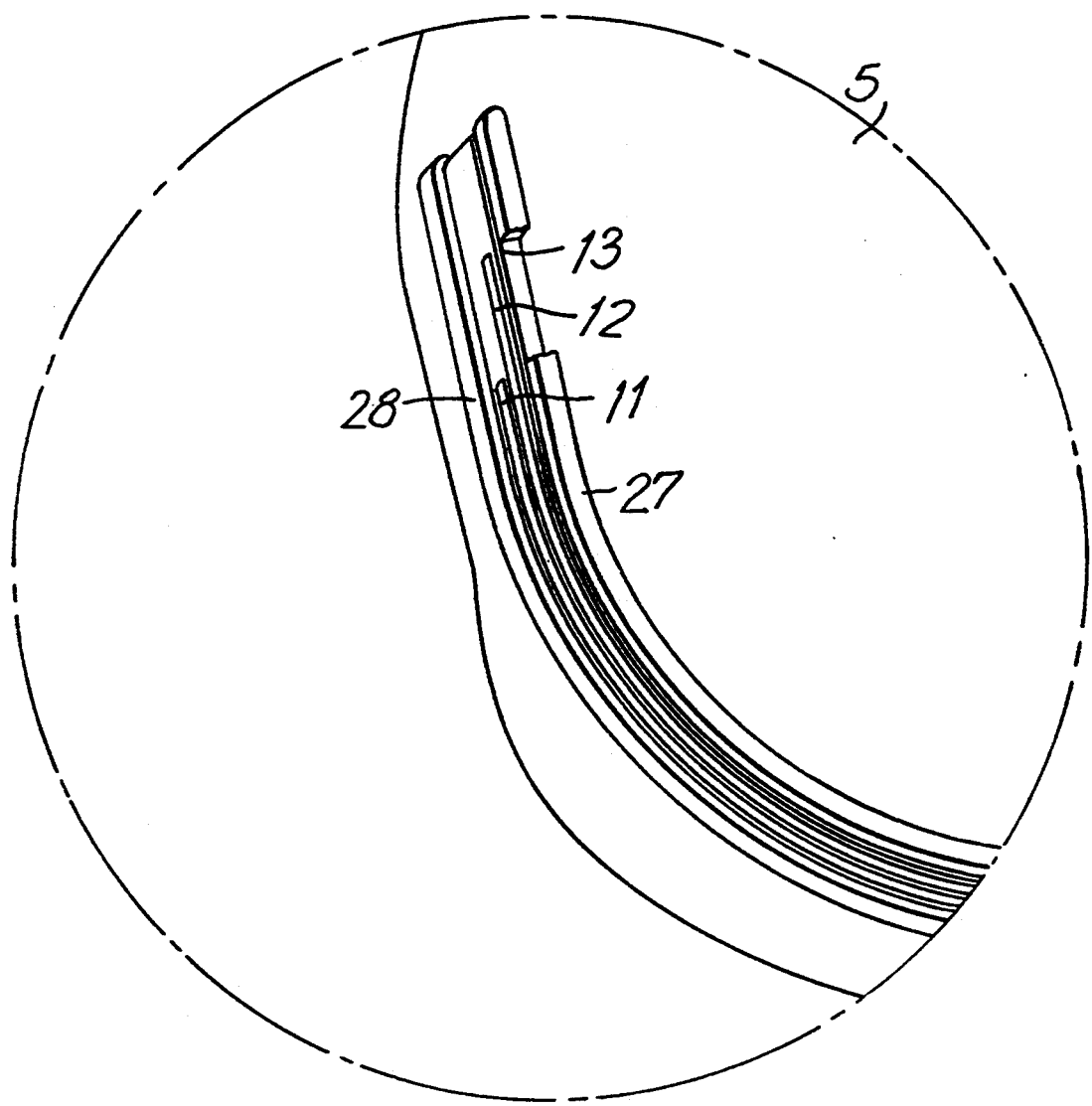
FIG. 11 is an enlarged scale view of the wall of an inflated balloon of an embodiment having a movable thermocouple assembly.

FIG. 11 illustrates an embodiment having a thermocouple assembly which is movable relative to the wall of the inflatable compliant balloon. The thermocouple assembly comprises three thermocouples 11, 12 and 13 similar to those illustrated in FIG. 1 slidably mounted in a track defined by grooved side rails 27, 28. The thermocouple assembly may be moved backward or forward along the track, if required, until a maximum temperature reading is obtained.

Monitoring of the rectal mucosal temperature, which gives an accurate determination of the temperature of the prostate tissue, may be commenced when the prostate is thermally treated with radiant energy, for example, from a conventional microwave antenna inserted in the prostatic urethra.

Use of the rectal probe according to the invention provides simultaneous temperature sensing and cooling of the anterior rectal wall during simultaneous heating of the prostate.

We claim:

1. Rectal probe for sensing and monitoring a patient's rectal mucosal temperature comprising a catheter having a longitudinal axis, a proximal end and a distal portion terminating in a distal end, an inflatable, low pressure, compliant balloon mounted along said longitudinal axis within said distal portion, a temperature element associated with a side of the balloon wall with leads from said element attached to a connector located at the proximal end of the catheter, means for holding the probe at a proper position within a patient's rectum and means for inflating the balloon, the balloon being inflated when it is properly positioned to put the temperature element in intimate contact with the anterior side of the rectum, the sensing and monitoring means of the probe consisting solely of the combination of said inflated balloon and said temperature element.

2. A probe according to claim 1, in which the temperature element is directly attached to the wall of the balloon.

3. A probe according to claim 1, in which the temperature element is movably associated with the balloon wall.

4. A probe according to claim 1, in which the temperature element is a thermocouple assembly adapted to monitor rectal mucosal temperature during thermal treatment of the patient's prostate.

5. A probe according to claim 4, in which said thermocouple assembly comprises three thermocouples in spaced-apart relationship.

6. A probe according to claim 1 which includes a hollow tube with an open distal end located along the longitudinal axis.

7. A probe according to claim 1, in which the means for holding the probe within the patient's rectum is a side arm attached to a housing enveloping a portion of the catheter proximal to the anal sphincter when the compliant balloon is properly positioned for inflation within the rectum.

8. A probe according to claim 7, in which the side arm is attached to the housing through a longitudinally-movable collar and a lock which enables the arm to be locked in place and taped against the patient's leg when the probe is properly positioned in the patient's rectum.

9. A probe according to claim 1, in which the means for holding the probe within the patient's rectum is a location balloon mounted on the catheter in a position proximal to the inflatable, low pressure, compliant balloon so that it is adapted to be located outside the rectum against the entrance to the rectum when the inflatable compliant balloon is properly positioned in the rectum.

10. A probe according to claim 1, in which the means for holding the probe within the patient's rectum is a movable tab mounted on the catheter in a position proximal to the inflatable, low pressure, compliant balloon.

11. A probe according to claim 1, which includes means for providing circulating coolant to the interior of the low pressure, inflatable, compliant balloon.

12. A probe according to claim 1, in which the inflatable compliant balloon is contained within the catheter and, when inflated, is adapted to be deployed beyond the distal end of the catheter.

13. A process for monitoring a patient's rectal mucosal temperature during thermal treatment of the patient's prostate which comprises inserting a rectal probe in the patient's rectum, which probe comprises a catheter having a longitudinal axis, a proximal end and a distal portion terminating in a distal end, an inflatable, low pressure, compliant balloon mounted along said longitudinal axis within said distal portion, a temperature element associated with a side of the balloon wall with leads from said element attached to a connector located at the proximal end of the catheter, means for holding the probe at a proper position within a patient's rectum and means for inflating the compliant balloon, properly positioning the rectal probe so that the temperature element comes into intimate contact with the anterior side of the rectum when the balloon is inflated; inflating the balloon; irradiating the patient's prostate with radiant energy; monitoring the rectal mucosal temperature on the anterior side of the rectum and modulating the radiant energy to prevent over heating leading to rectal injury when a predetermined maximum rectal mucosal temperature is reached.

14. A process according to claim 13, in which the temperature element is a thermocouple assembly comprising three thermocouples in spaced-apart relationship.

15. A process according to claim 14, in which proper positioning of the rectal probe is determined by adjusting the position of the thermocouple assembly until a maximum temperature reading is provided.

* * * * *